(12) United States Patent
Dohta

(10) Patent No.: US 7,398,161 B2
(45) Date of Patent: Jul. 8, 2008

(54) SAMPLING METHOD AND SAMPLING DEVICE, AND LOGD MEASURING METHOD AND LOGD MEASURING SYSTEM

(75) Inventor: Yukifumi Dohta, deceased, late of Ibaraki (JP); by Satomi Horiike, legal representative, Osaka (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 11/663,096

(22) PCT Filed: Sep. 13, 2005

(86) PCT No.: PCT/JP2005/016841

§ 371 (c)(1),
(2), (4) Date: Jun. 13, 2007

(87) PCT Pub. No.: WO2006/030784

PCT Pub. Date: Mar. 23, 2006

(65) Prior Publication Data

US 2007/0255507 A1    Nov. 1, 2007

(30) Foreign Application Priority Data

Sep. 15, 2004    (JP)    ............................. 2004-268600

(51) Int. Cl.
*C12M 1/34*    (2006.01)
(52) U.S. Cl. ..................... 702/25; 435/287.1; 435/176; 435/177; 435/4; 435/817; 73/863.53; 73/863.52; 73/863.54

(58) Field of Classification Search .................. 702/25; 435/287.1, 176, 177, 4, 817; 73/863.53, 73/863.52, 863.54; 119/14.14; 422/102, 422/100, 103, 73, 99; 436/180, 69
See application file for complete search history.

(56) References Cited

U.S. PATENT DOCUMENTS 5,423,966 A * 6/1995 Wiktorowicz ............... 204/453

(Continued)

FOREIGN PATENT DOCUMENTS

JP    63-175765    7/1988

(Continued)

OTHER PUBLICATIONS

International Search Report for PCT/JP2005/016841 mailed Dec. 20, 2005.

(Continued)

*Primary Examiner*—Carol S Tsai
(74) *Attorney, Agent, or Firm*—Darby & Darby

(57) ABSTRACT

A sampling method sampling a lower-layer liquid from a liquid body comprised of two layers of liquids, an upper-layer liquid (octanol) and the lower-layer liquid (buffer solution), without mixing the layers. An extracting device is provided with a tubular apical end and is adapted to bring the apical end from above into a liquid to extract the liquid through the apical end. The method includes a plug injection step of injecting a plug liquid without mixing with the upper-layer liquid 50*a*, into the apical end 11*a* of the extracting device, and an extraction step of extracting the lower-layer liquid with the plug liquid by means of the extracting device.

8 Claims, 7 Drawing Sheets

U.S. PATENT DOCUMENTS

| | | | |
|---|---|---|---|
| 6,406,922 B2 * | 6/2002 | Casterlin et al. | 436/518 |
| 6,694,830 B2 * | 2/2004 | Hakes | 73/863.53 |
| 6,709,856 B2 * | 3/2004 | Matsumoto et al. | 435/287.1 |
| 7,074,431 B2 * | 7/2006 | Busson et al. | 424/484 |
| 2001/0035349 A1 * | 11/2001 | Matsumoto et al. | 204/403 |
| 2004/0009261 A1 * | 1/2004 | Brody | 426/34 |

FOREIGN PATENT DOCUMENTS

| | | |
|---|---|---|
| JP | 2001-124756 | 5/2001 |
| JP | 3295014 | 4/2002 |
| JP | 3351615 | 9/2002 |
| JP | 3444872 | 6/2003 |
| JP | 3523207 | 2/2004 |

OTHER PUBLICATIONS

ElogDoct: A Tool for Lipophilicity Determination in Drug Discovery.2.Basic and Neutral Compounds: by Lombardo et al., J. Med. Chem. 2001, 44, pp. 2490-2497.

International Preliminary Report on Patentability dated Mar. 20, 2007 issued during the prosecution of International Patent Application No. PCT/JP2005/016841.

* cited by examiner

US 7,398,161 B2

SAMPLING METHOD AND SAMPLING DEVICE, AND LOGD MEASURING METHOD AND LOGD MEASURING SYSTEM

CROSS-REFERENCE TO RELATED APPLICATIONS

The present application is a national stage application under U.S.C. §371 of International Application No. PCT/JP2005/016841, which was filed on Sep. 13, 2005, which designated the United States of America and which claims priority of Japanese Patent Application No. P2004-268600, which was filed on Sep. 15, 2004. Each of International Application No. PCT/JP2005/016841 and Japanese Patent Application No. P2004-268600 is hereby incorporated in its entirety herein. The International Application was published in Japanese on Mar. 23, 2006 as WO 2006/030784 A1 under PCT Article 21(2).

FIELD OF THE INVENTION

The present invention relates to a sampling method for sampling a liquid, a sampling apparatus, and a logD measuring method and logD measuring system based on the sampling method.

BACKGROUND OF THE INVENTION

Concerning many medical products, absorbability, metabolizability, solubility, etc. of a drug are associated with hydrophobicity of a compound used as the drug. There is a conventional technique of determining logD (water-octanol partition coefficient) as an index to indicate the hydrophobicity of a compound (e.g., cf. Patent Documents 1-3 below).
Patent Document 1: Japanese Patent Application Laid-Open No. 2001-124756
Patent Document 2: Japanese Patent No. 3444872
Patent Document 3: Japanese Patent No. 3523207

A method of determining logD is to calculate logD on the basis of a retention time in HPLC (High Performance Liquid Chromatography), as described in Patent Documents 1-3 above. However, this method obtains the calculated logD as an estimate value, and thus has a problem that it is more likely to produce an error than a method using actually measured values as described below.

Another method of determining logD is a shake-flask method. The shake-flask method is to put a compound as a measured object, water, and octanol in a flask, to shake the mixture, to measure a concentration of the compound in water and a concentration of the compound in octanol, and to calculate logD on the basis of the measured values.

The shake-flask method involves the step of measuring the concentrations in the respective solutions, which may be a method of separating water and octanol and measuring the concentrations in the separate solutions. However, this separating operation is cumbersome and does not suit lump-sum handling of multiple analytes. The separating operation originally involves adsorption on a container or the like and could cause error.

There is another method of sampling each of an aqueous solution and octanol by means of a liquid handler or the like. However, since the water layer is located below the octanol layer, this method normally has a problem that octanol is mixed in the aqueous solution during sampling thereof to cause contamination. Particularly, when logD is a large value in the range of about 4-6, the concentration in the aqueous solution is $1/10^4$ to $1/10^6$ of the concentration in octanol, and mixing of a small amount of octanol will pose a serious problem in the calculation of logD.

SUMMARY OF THE INVENTION

The present invention has been accomplished in order to solve the problems as describe above, and an object of the invention is to provide a sampling method and sampling apparatus capable of sampling a lower-layer liquid from a liquid body comprising of two layers of two types of liquids, without mixing and without difficulties, and a logD measuring method and logD measuring system based on the sampling method.

In order to achieve the above object, a sampling method according to the present invention is a sampling method of sampling a lower-layer liquid from a liquid body comprised of two layers of liquids, an upper-layer liquid and the lower-layer liquid, using extracting means provided with a tubular apical end and adapted to bring the apical end from above into a liquid and to extract the liquid through the apical end, the sampling method comprising: a plug injection step of injecting a plug liquid not mixing with the upper-layer liquid, into the apical end of the extracting means; and an extraction step of extracting the lower-layer liquid by means of the extracting means with the plug liquid injected in the plug injection step.

In this sampling method, the plug injection step is to inject the plug liquid into the apical end of the injecting means. In the subsequent extraction step, the extracting means is brought into the liquid body in order to extract the lower-layer liquid, and the plug liquid repels the upper-layer liquid to prevent it from mixing into the injecting means, during passage of the apical end of the extracting means through the upper-layer liquid. Namely, this method prevents occurrence of contamination by the upper-layer liquid during the extraction of the lower-layer liquid. In addition, the injection of the plug liquid is also readily carried out, thus enabling easy sampling.

Preferably, the upper-layer liquid is octanol in which a predetermined chemical substance is dissolved, the lower-layer liquid is a buffer solution in which the predetermined chemical substance is dissolved, and the plug liquid is the buffer solution. This configuration permits us to readily perform the sampling of the solution for calculation of logD or the like, without mixing of octanol.

A logD measuring method according to the present invention is a logD measuring method of sampling a buffer solution from a liquid body comprised of two layers of liquids, an upper layer of octanol in which a predetermined chemical substance is dissolved, and a lower layer of the buffer solution in which the predetermined chemical substance is dissolved, using extracting means provided with a tubular apical end and adapted to bring the apical end from above into a liquid and to extract the liquid through the apical end, and measuring a logD of the chemical substance, the logD measuring method comprising: a plug injection step of injecting a plug liquid not mixing with the octanol, into the apical end of the extracting means; an extraction step of extracting the buffer solution by means of the extracting means with the plug liquid injected in the plug injection step; an in-buffer concentration measuring step of measuring a concentration of the chemical substance in the buffer solution extracted in the extraction step; and a logD calculation step of calculating the logD on the basis of the concentration measured in the in-buffer concentration measuring step.

This logD calculating method is arranged to measure the concentration of the chemical substance in the buffer solution sampled by the above sampling method and to calculate the logD on the basis of the measured concentration. Since this method allows easy sampling of the buffer solution without occurrence of the contamination as described above, the concentration of the chemical substance in the buffer solution can be accurately measured. Accordingly, the logD can be calculated readily and accurately. The buffer solution herein is one medium into which the chemical substance is dissolved during the measurement of logD and the buffer solution suitably applicable is, for example, water, phosphoric acid aqueous solution, or the like.

Preferably, a mass spectrometer is used to measure the concentration in the in-buffer concentration measuring step. This configuration permits us to accurately measure the concentration even if the concentration of the chemical substance is low in the buffer solution, and thus permits us to calculate accurate logD, particularly, even if logD is a large value in the range of approximately 4-6.

Preferably, the logD measuring method further comprises an in-octanol concentration measuring step of measuring a concentration of the chemical substance in the octanol, and the logD calculation step comprises calculating the logD on the basis of the concentrations measured in the in-buffer concentration measuring step and in the in-octanol concentration measuring step. This configuration permits us to calculate accurate logD on the basis of an actually measured value of the concentration in octanol.

Preferably, the in-octanol concentration measuring step comprises extracting and diluting the octanol, and measuring a concentration of the chemical substance in the diluted octanol with a mass spectrometer, thereby measuring the concentration of the chemical substance. This configuration permits us to calculate accurate logD, for example, even if the concentration in octanol is higher than the concentration in the buffer solution.

While providing the invention of the above-described methods, the present invention also provides the invention of the sampling apparatus and logD measuring system as described below.

A sampling apparatus according to the present invention is an apparatus comprising extracting means provided with a tubular apical end and adapted to bring the apical end from above into a liquid and to extract the liquid through the apical end; plug injecting means for injecting a plug liquid not mixing with the upper-layer liquid, into the apical end of the extracting means; and extraction controlling means for controlling the extracting means with the plug liquid injected by the plug injecting means, so as to extract the lower-layer liquid.

A logD measuring system according to the present invention is a logD measuring system for sampling a buffer solution from a liquid body comprised of two layers of liquids, an upper layer of octanol in which a predetermined chemical substance is dissolved, and a lower layer of the buffer solution in which the predetermined chemical substance is dissolved, and measuring a logD of the chemical substance, the logD measuring system comprising: extracting means provided with a tubular apical end and adapted to bring the apical end from above into a liquid and to extract the liquid through the apical end; plug injecting means for injecting a plug liquid not mixing with the octanol, into the apical end of the extracting means; extraction controlling means for controlling the extracting means with the plug liquid injected by the plug injecting means, so as to extract the buffer solution; in-buffer concentration measuring means for measuring a concentration of the chemical substance in the buffer solution extracted in the control by the extraction controlling means; and logD calculating means for calculating the logD on the basis of the concentration measured by the in-buffer concentration measuring means.

According to the present invention, the plug liquid repels the upper-layer liquid to prevent it from mixing into the injecting means, whereby occurrence of contamination by the upper-layer liquid is prevented during the extraction of the lower-layer liquid. In addition, the injection of the plug liquid is also readily carried out, thus enabling easy sampling.

DETAILED DESCRIPTION OF THE INVENTION

Figure 1:
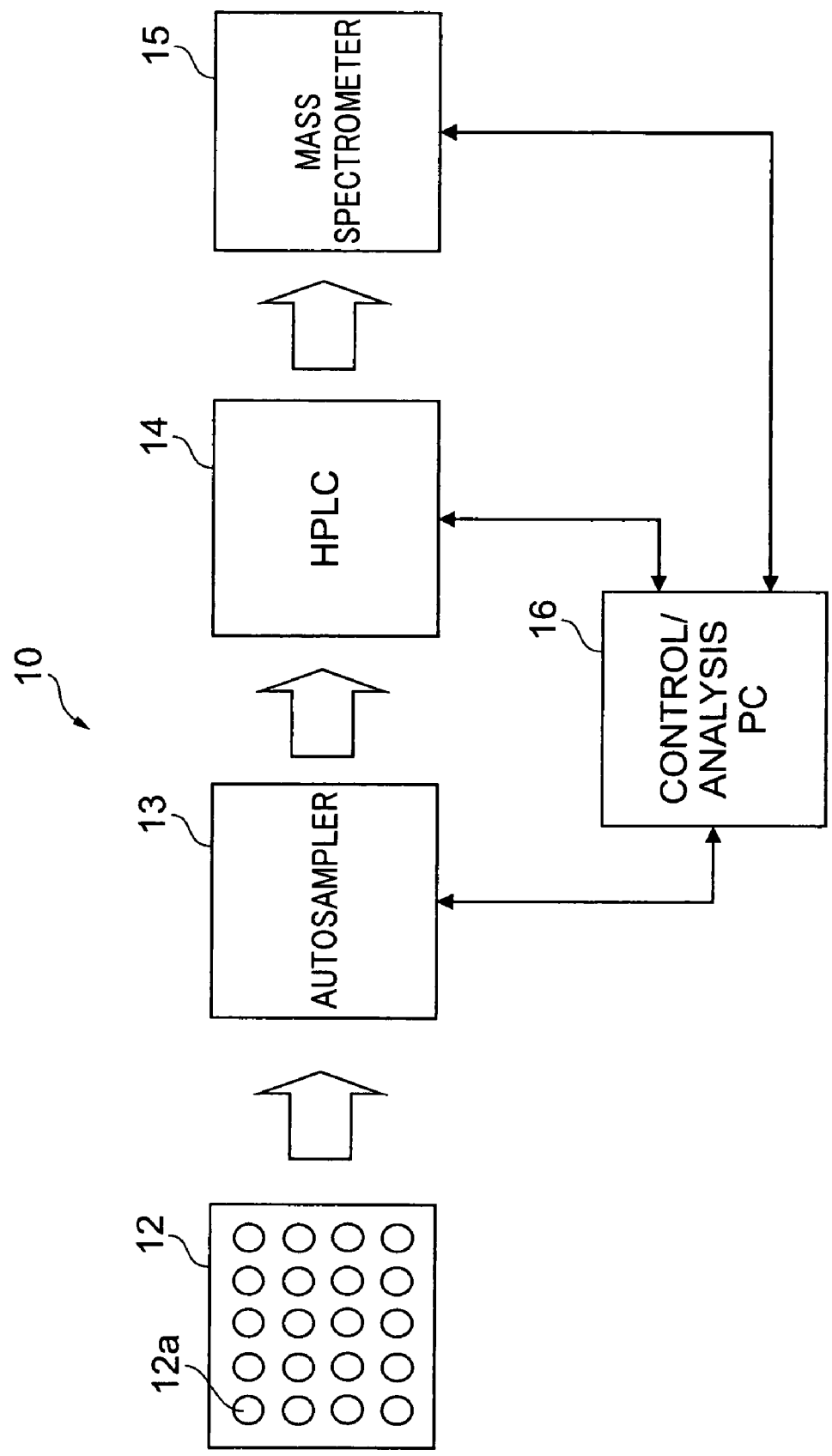
FIG. 1 is a drawing schematically showing a configuration of a logD measuring system in an embodiment of the present invention.

The following reference numerals identify elements which are illustrated in the drawings and further described herein: 10 measuring system; 11 syringe; 11a needle; 12 well plate; 12a wells; 13 autosampler; 14 HPLC; 15 mass spectrometer; 16 PC for control and analysis; 50a octanol; 50b buffer solution; 51 plug liquid.

BEST MODE FOR CARRYING OUT THE INVENTION

The present invention will be described below in detail with reference to the drawings. In the description of the drawings, the same elements will be denoted by the same reference elements, without redundant description. It is noted that dimensional ratios in the drawings do not always agree with those in the description.

FIG. 1 is a drawing schematically showing a configuration of an embodiment of logD measuring system 10 according to the present invention. The logD measuring system 10 is adapted to measure logD of a chemical substance such as a compound by actually measuring concentrations of the compound dissolved in a buffer solution and in octanol. For actually measuring the concentrations, the buffer solution and octanol in which the compound is dissolved are extracted. The buffer solution herein is one medium into which the compound is dissolved on the occasion of the measurement of logD, and the buffer solution suitably applicable is, for example, water, phosphoric acid aqueous solution, or the like. Values of logD differ depending upon pH and, for example, where logD is measured for a pharmaceutical purpose, the buffer solution preferably applicable is a liquid with pH of 7.4 equal to that of the biological fluid of human body. For example, a phosphoric acid aqueous solution with pH of 7.4 can be prepared, for example, from $NaH_2PO_4$ aqueous solution and $Na_2HPO_4$ aqueous solution. A concentration of the phosphoric acid aqueous solution used as the buffer solution is preferably approximately 10-200 mM.

When logD takes a large value in the range of approximately 4-6, as described above, the concentration in the buffer solution is $1/10^4$ to $1/10^6$ of the concentration in octanol and mixing of a small amount of octanol during extraction of the buffer solution will pose a serious problem in the calculation of logD. For example, supposing the buffer solution is extracted by 2.5 μl as described later, 10% contamination is assumed to be accepted. When logD of the compound is 4, the concentration in the buffer solution is $1/10^4$ of the concentration in octanol. An acceptable amount of octanol mixed in this case is calculated according to extracted amount (2.5 μl)× concentration ratio ($1/10^4$)×acceptance rate (10%) and is as small as 25 pl. Therefore, the present system 10 requires adequate prevention of mixing of octanol during the extraction of the buffer solution.

The configuration of the logD measuring system 10 will be described below. As shown in FIG. 1, the logD measuring system 10 comprises well plate 12, autosampler 13, HPLC 14, mass spectrometer 15, and PC (Personal Computer) 16 for control and analysis.

The well plate 12 is provided with a plurality of wells 12a so as to be able to retain a liquid, and is used for preparing and retaining a sample for measurement of logD, which consists of two layers of an octanol layer and a buffer solution layer, in the wells 12a. The wells 12a are preferably, for example, ninety six wells, for simultaneously preparing and retaining samples of multiple analytes.

Figure 3:
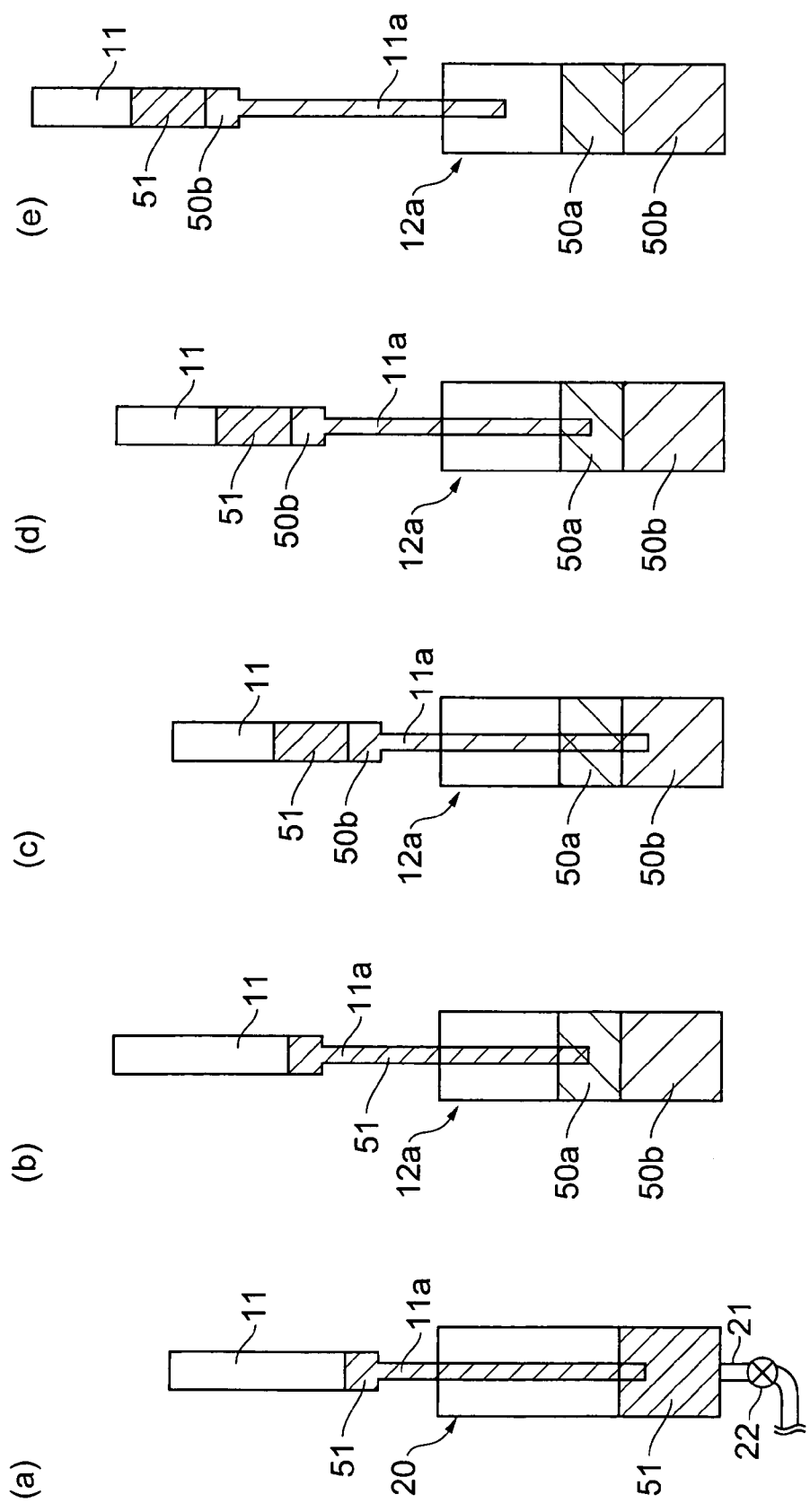
FIG. 3 is a drawing schematically showing each of phases of sampling.

The autosampler 13 is an extracting means for extracting a liquid retained in a well 12a of the well plate 12 placed at a predetermined position. The extracted liquid (sample) is automatically fed to HPLC 14, for analysis with HPLC 14 and mass spectrometer 15. The autosampler 13 is equipped with a syringe 11 and, as shown in FIG. 3, the syringe 11 is provided with a needle 11a which is a tubular apical end for extraction of a liquid. The syringe 11 is adapted to bring the needle 11a from above into a liquid and to extract the liquid through the needle 11a. The needle 11a herein is preferably one having the inside diameter of several tenths of a millimeter and the length of several ten millimeters. The syringe 11 can extract an accurate amount of a liquid in μl unit under control from the control/analysis PC 16. The autosampler 13 applicable is, specifically, for example HTS PAL available from CTC Analytics AG.

The HPLC 14 separates a sample fed from the autosampler 13 and feeds separated fractions to the mass spectrometer 15. The HPLC 14 applicable is, specifically, for example Alliance 2690 available from Waters Corporation.

The mass spectrometer 15 measures a quantitative value of an amount of a compound contained in a sample. Specifically, it measures the quantitative value on the basis of a value of a peak corresponding to a mass of the compound. The measured data is transmitted to the control/analysis PC. The ionization voltage in the mass spectrometer 15 is preferably preliminarily set to an appropriate value before measurement of logD, using an adjustment sample such as an acetonitrile solution of the compound as a measured object. The mass spectrometer 15 applicable is, specifically, for example ZQ2000 available from Waters Corporation.

The control/analysis PC 16 controls the autosampler 13, HPLC 14, and mass spectrometer 15. How each device is controlled to operate will be described later. These controls are preferably carried out using control programs and software applications. The control/analysis PC 16 calculates a concentration from the quantitative value of the amount of the compound acquired by the mass spectrometer 15 and calculates logD from the concentration. A specific calculation method will be described later. The HPLC 14, mass spectrometer 15, and control/analysis PC 16 correspond to each concentration measuring means for measuring the concentrations of the compound in the buffer solution and in octanol. The control/analysis PC 16 corresponds to the logD calculating means for calculating logD from the measured concentrations.

Figure 2:
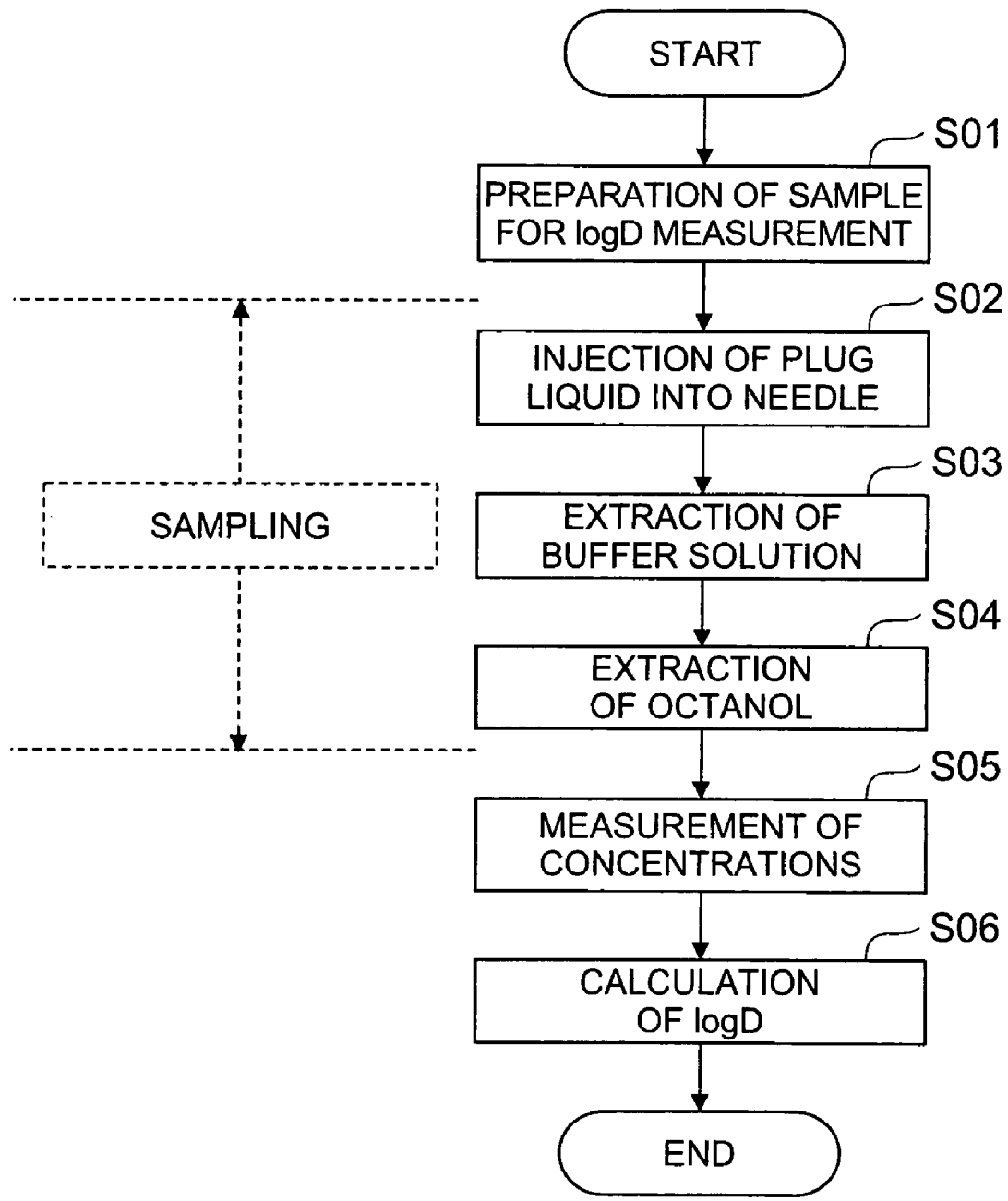
FIG. 2 is a drawing showing a flow of processes in a sampling method and logD measuring method in an embodiment of the present invention.

The following will describe an embodiment of a sampling method and logD measuring method according to the present invention, using the logD measuring system 10, with reference to the flowchart shown in FIG. 2.

The first step is to prepare a sample for measurement of logD as follows (S01). This sample is one obtained by dissolving a compound as a measured object for logD into a buffer solution and octanol to obtain two separate layers. The compound as a measured object is preferably preliminarily dissolved in a predetermined concentration of 1 mM or 10 mM or the like in DMSO (Dimethyl Sulfoxide) before the preparation of the sample. This is for facilitating dissolution of the compound in octanol and in the buffer solution.

For preparation of the sample, DMSO with the compound dissolved therein is first dispensed by a predetermined fractional amount such as 10 μl into each of wells 12a of the well plate 12, using a pipette. The pipette is preferably one enabling extraction and addition of an accurate amount of a liquid in μl unit, under control of a microprocessor provided for the pipette. The pipette is preferably provided with a plurality of channels in order to allow simultaneous extraction of samples of multiple analytes.

The subsequent step is to add a predetermined amount of octanol, e.g. 300 μl, into each well 12a of well plate 12 with a pipette. Thereafter, preferably, each well 12a is closed with a well cap or the like and the well plate 12 is subjected to agitation and centrifugation. Since DMSO is more soluble in the buffer solution than in octanol, it is preliminarily dissolved in octanol. This is for enabling measurement of accurate logD. The agitation is intensively carried out, for example, at room temperature for five minutes with a shaker. The centrifugation is carried out, for example, at 2000 rpm for five minutes with a centrifuge after the agitation.

The next step is to remove the cap from the well plate 12 and to add a predetermined amount of a buffer solution, e.g. 600 μl, into each well 12a with a pipette. Thereafter, each well 12a is again closed with a cap and the well plate 12 is subjected to agitation and centrifugation. The agitation is intensively carried out, for example, at room temperature for one hour with a shaker. The centrifugation is carried out, for example, at 2000 rpm for five minutes with a centrifuge after the agitation. After completion of the above treatments, a sample for measurement of logD consisting of an upper octanol layer 50a and a lower buffer solution layer 50b separated is obtained, as shown in FIG. 3(b), in each well 12a.

The subsequent steps are to sample the octanol 50a and buffer solution 50b for measurement of concentrations (S02-S04). First, the sampling of buffer solution 50b will be described with reference to FIG. 3. The well plate 12 with the prepared sample in the well 12a is located at a predetermined position and in an uncapped state in the autosampler 13. Under control from the control/analysis PC 16, the autosampler 13 injects a predetermined amount of plug liquid 51 into the syringe 11 from a wash port 20 located at a position different from that of the well plate 12 and also being a container, as shown in FIG. 3(a) (S02, plug injection step). This injection results in bringing the needle 11a of the syringe 11 into a state in which it contains the plug liquid 51, as shown in FIG. 3(a). The aforementioned predetermined amount is an appropriate amount, e.g., 2.5 μl. As shown in FIG. 3, a tube 21 is connected to a bottom part of the wash port 20. The tube 21 is provided with an electromagnetic valve 22, and the liquid in the wash port 20 can be replaced with another through the tube 21 before and after a cleaning step described below, by switching of this electromagnetic valve 22.

The plug liquid 51 is a liquid for preventing the upper-layer octanol 50a from mixing into the syringe 11 during extraction of the lower-layer buffer solution 50b. The plug liquid 51 is a liquid not mixing with the upper-layer octanol 50a. Specifically, the plug liquid preferably applicable is, for example, water or phosphoric acid aqueous solution. Namely, it is preferable to use the same as the buffer solution 50b (in which no compound is dissolved). The control/analysis PC 16 in this step functions as plug injection (control) means for performing such control as to inject the plug liquid into the needle 11a as an apical end of the extracting device.

A subsequent step is to extract the lower-layer buffer solution through the syringe 11 with the plug solution injected in the needle 11a (S03, extraction step). This extraction is carried out so that the autosampler 13 under control from the control/analysis PC 16 puts the needle 11a of the syringe 11 into the well 12a with the sample therein, as shown in FIG. 3(b)-(e). Since the needle 11a is kept in a state in which it contains the plug liquid 51, during passage of the needle 11a through the octanol layer 50a, as shown in FIG. 3(b), the plug liquid 51 repels the octanol 50a to prevent the octanol 50a from mixing into the syringe 11. After the needle 11a is put in the buffer solution layer 50b, as shown in FIG. 3(c), a predetermined amount of buffer solution 50b is extracted through the needle 11a. After completion of this extraction, the needle 11a is brought into a state in which it contains the buffer solution 50b. The predetermined amount is an appropriate amount, e.g., 2.5 μl.

Subsequently, the needle 11a is pulled out through the octanol layer 50a, as shown in FIG. 3(d); during this step the needle 11a is in a state in which it contains the buffer solution 50b, and thus the buffer solution 50b repels the octanol 50a to prevent the octanol 50a from mixing into the syringe 11. Since the octanol 50a and buffer solution 50b have the properties of being separated in two layers, the buffer solution 50b can repel the octanol 50a as described above. Subsequently, the needle 11a is pulled out of the sample as shown in FIG. 3(e). After the needle is pulled out of the sample, the circumference of the needle 11a is washed with water, ethanol, or the like in the wash port 20 to prevent occurrence of contamination by the octanol 50a attached to the circumference of the needle 11a. The buffer solution 50b thus sampled is automatically fed to HPLC 14. The control/analysis PC 16 in this step functions as extraction controlling means for controlling the extracting device to extract the buffer solution 50b.

The plug liquid 51 and the buffer solution 50b are normally mixed with each other without separating in two layers as shown in FIG. 3 (they are depicted as separated in two layers in FIG. 3 for easier understanding of description), but there is no change in the amount of the compound contained in the extracted buffer solution layer 50b; therefore, the concentration in the buffer layer can be measured.

Sampling of octanol 50a will be described below. Since the octanol layer 50a is the upper layer, it is extracted with a pipette or the like, without any possibility of contamination during the extraction (S04). Incidentally, the concentration of the compound in octanol 50a is higher than that in the buffer solution 50b. For example, when logD is 4, as described above, the concentration of the compound in octanol is 1000 times higher than the concentration of the compound in the buffer solution 50b. Therefore, in order to avoid ionic saturation in the mass spectrometer 15, it is preferable to dilute the extracted octanol 50a with a solvent for dilution such as ethanol. For implementing accurate measurement even in cases where logD takes a high value in the range of 4-6, the dilution is preferably carried out, for example, in the order of several thousand times. The diluted octanol 50a is put into another well plate, is extracted by the autosampler 13 in the same manner as the extraction of the buffer solution, and is automatically fed to the HPLC 14. The sampling of the buffer solution 50b does not have to be carried out first, but the sampling of the octanol 50a may be first carried out.

A subsequent step is to measure concentrations of the compound as an object for measurement of logD in the octanol 50a and in the buffer solution 50b extracted from the well 12a and fed to the HPLC 14, using the HPLC 14 and mass spectrometer 15 (S05, in-buffer concentration measuring step and in-octanol concentration measuring step). The measurement of concentrations is carried out, specifically, by calculating a quantitative value of the amount of the compound contained in each solution, from a peak value corresponding to the compound in spectral data acquired by the mass spectrometer 15. Information processing including the calculation of quantitative value is carried out in the control/analysis PC 16. The concentrations in the octanol 50a and in the buffer solution 50b are measured at different timings.

The measurement of the concentrations in the respective solutions in S05 may also be carried out by a measuring method based on absorbance of UV (Ultra Violet), for example, instead of the method using the mass spectrometer 15 as described above.

Subsequently, the control/analysis PC 16 calculates logD from the measured concentrations, using the following equation (S06, logD calculation step).

$$\log D = \log ([\text{concentration in octanol layer}]/ \quad [1]$$
$$[\text{concentration in buffer solution layer}])$$
$$= \log ([\text{concentration in diluted octanol} \times \text{dilution rate}]/$$
$$[\text{concentration in buffer solution layer}])$$

As described above, the present embodiment uses the plug liquid 51 to prevent occurrence of contamination by the upper-layer octanol 50a during the extraction of the lower-layer buffer solution 50b. The sampling method in the present embodiment also permits easy injection of the plug liquid, thus enabling easy sampling. In addition, contamination is prevented well, so as to enable accurate concentration measurement. Therefore, logD can be calculated readily and accurately. Since the present embodiment can be readily carried out and enables the automation from sampling to measurement of logD as described above, it suits short-term analysis of multiple analytes, when compared with the conventional methods.

The two layers of liquids used for sampling do not always have to be those described above. The upper-layer liquid may be any nonaqueous solution in which a predetermined chemical substance, e.g., a chemical substance as an object for measurement of logD, is dissolved in a nonaqueous solvent. Specifically, the nonaqueous solvent is, for example, alkanol having four or more carbons. The lower-layer liquid may be an aqueous solution in which the aforementioned predetermined chemical substance is dissolved in an aqueous solvent. Specifically, the aqueous solvent is a liquid insoluble in the aforementioned nonaqueous solvent and is, for example, water or an aqueous solution in which a predetermined salt is dissolved. The plug liquid may also be the foregoing aqueous solvent.

Figure 4:
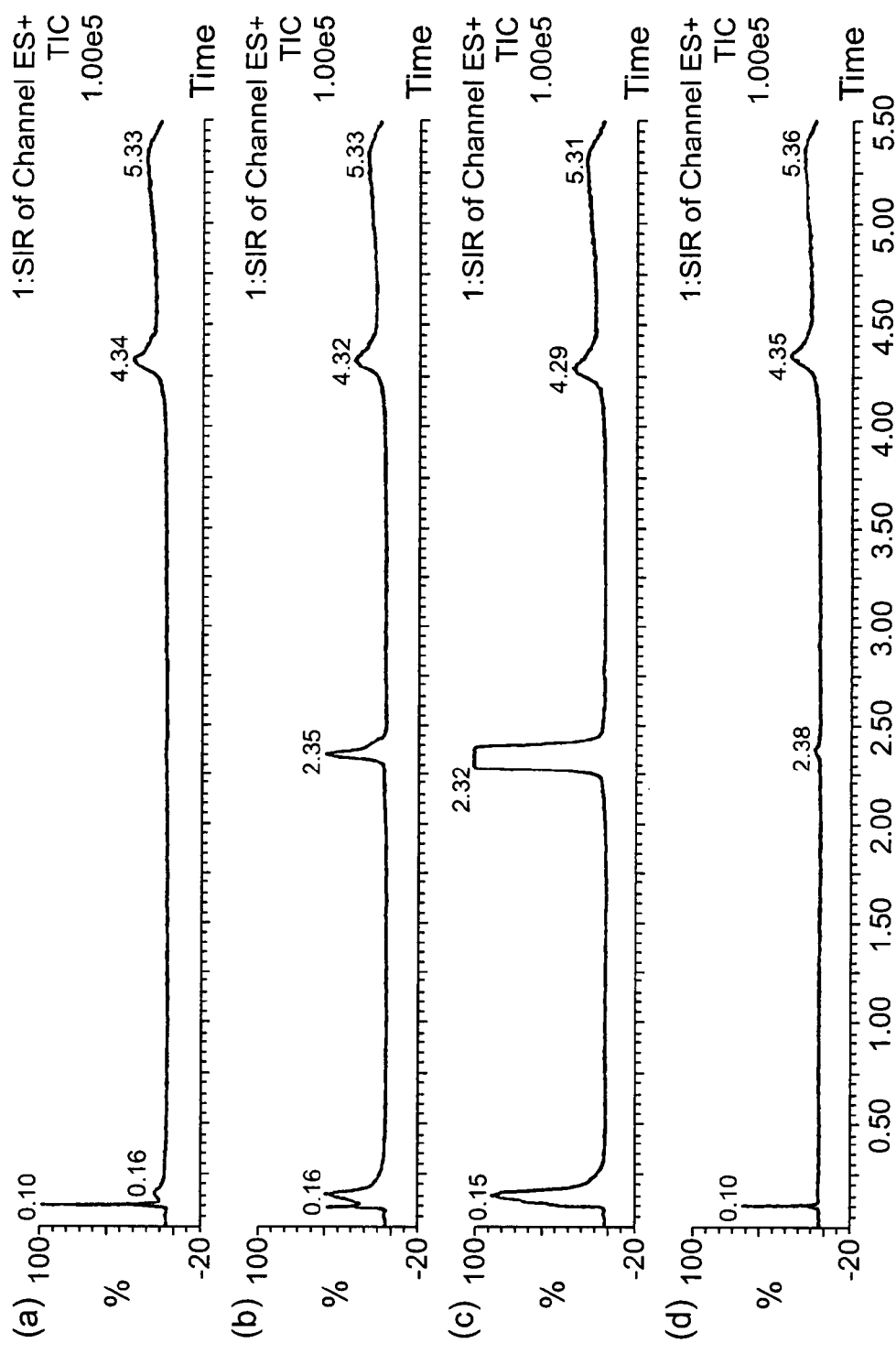
FIG. 4 is graphs of peaks from samples without use of a plug liquid which were separated by HPLC and measured by a mass spectrometer.
Figure 5:
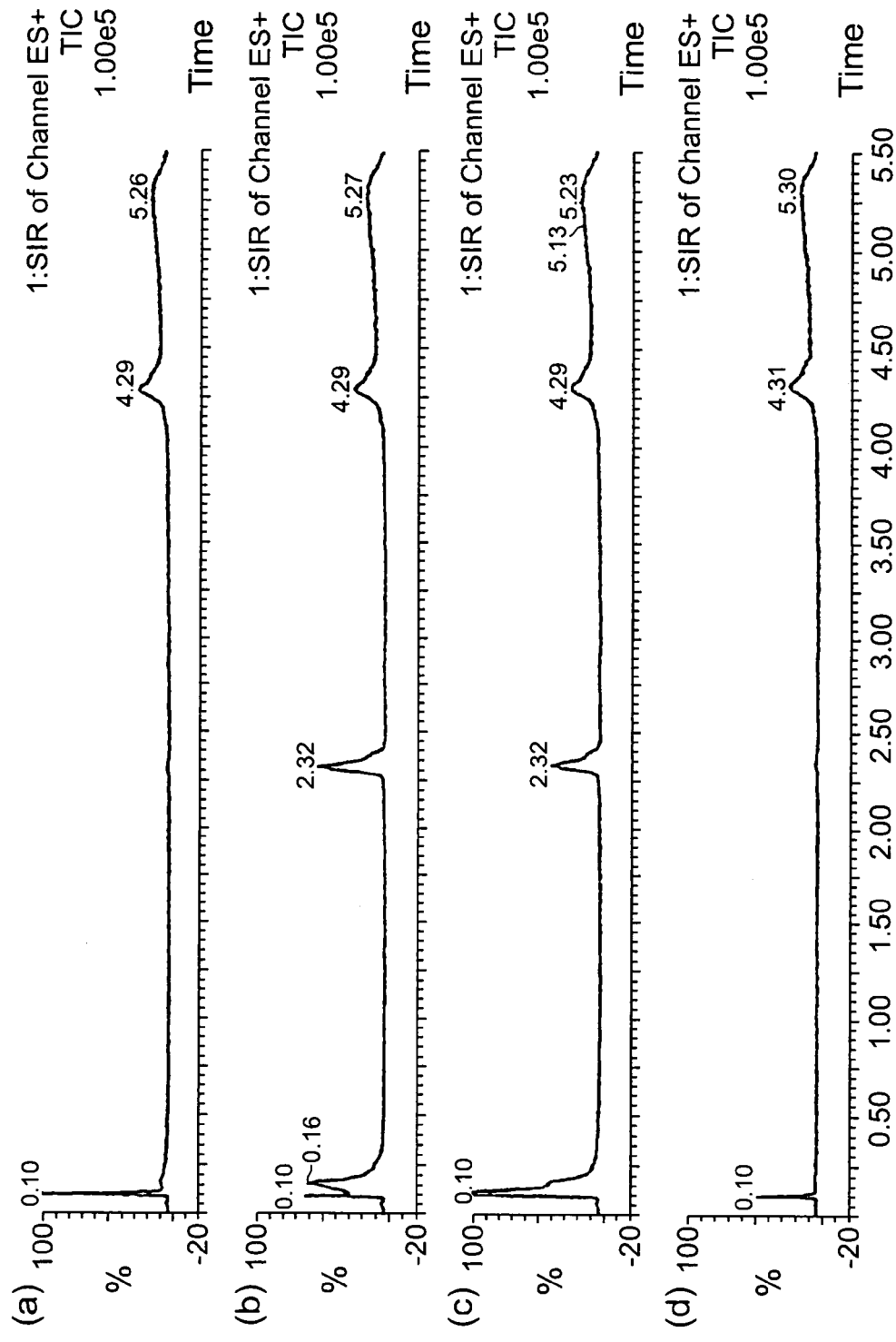
FIG. 5 is graphs of peaks from samples with use of a plug liquid which were separated by HPLC and measured by a mass spectrometer.

The following will describe that the present sampling method succeeds in prevention of contamination relative to the conventional methods, with reference to FIGS. 4 and 5. FIGS. 4 and 5 are chromatograms of samples separated by HPLC 14, and in each chromatogram the horizontal axis represents time while the vertical axis represents peak intensity measured. In FIGS. 4 and 5, (a) is a chromatogram in a case where nothing is fed to HPLC 14 (blank). (b) is a chromatogram in a case where an extract of buffer solution 50$b$ obtained by preliminarily removing only octanol layer 50$a$ from two layers of octanol layer 50$a$ and buffer solution layer 50$b$ prepared for measurement of logD is measured (i.e., a case where no contamination by octanol can occur). (c) is a chromatogram in a case where an extract of buffer solution 50$b$ from two layers of octanol layer 50$a$ and buffer solution layer 50$b$ as described above is measured. (d) is a graph in a blank case similar to (a). The chromatograms (a) to (d) are continuously measured using the same apparatus.

FIG. 4 illustrates chromatograms in cases using no plug liquid during the extraction of the buffer solution 50$b$ (corresponding to (c)) from the two layers of octanol layer 50$a$ and buffer solution layer 50$b$, and FIG. 5 the chromatograms in the cases using the plug liquid during the extraction (the cases of sampling as in the present embodiment). As seen from comparison between FIG. 4($a$) and FIG. 5($a$), comparison between FIG. 4($b$) and FIG. 5($b$), etc., the peaks in the time range of 2.32 to 2.35 correspond to the compound as a measured object. The peak at a time in the range of 2.32-2.35 has some width in FIG. 4($c$), whereas in FIG. 5($c$) the peak at a time in the range of 2.32 to 2.35 is of a shape similar to those in FIG. 4($b$) and FIG. 5($b$). This indicates that without use of the plug liquid (FIG. 4), contamination by octanol 50$a$ occurs and the compound contained in the octanol 50$a$ is also detected. On the other hand, with the use of the plug liquid (FIG. 5, in the case of the present embodiment), no contamination occurs by octanol 50$a$ and only the compound in the buffer solution 50$b$ is detected.

When the syringe 11 with the needle 11$a$ is used as the extracting device as in the present embodiment, it facilitates handling such as injection of plug liquid 51. Since the needle 11$a$ has the inside diameter of several tenths of a millimeter and the length of several ten millimeters, it facilitates retention of the plug liquid and enables surer prevention of contamination.

When the mass spectrometer 15 is used as in the present embodiment, the amount of the compound can be quantified, for example, even in cases where the concentration of the compound is low in the buffer solution, i.e., even in cases where the amount of the compound contained in the extract from the buffer solution is small, and logD can be accurately calculated.

Figure 6:
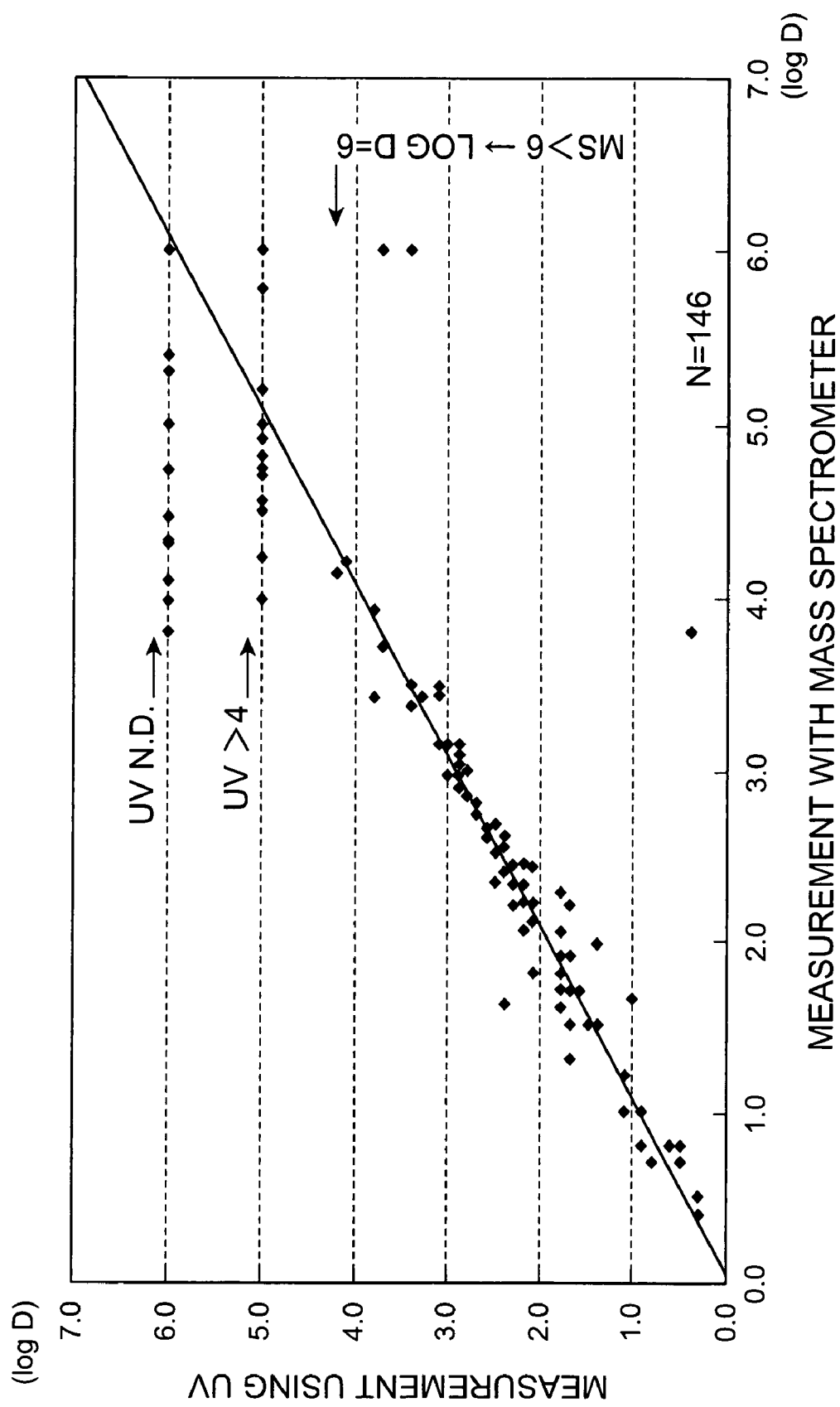
FIG. 6 is a scatter diagram of measured values of logD obtained by measurement of concentrations with a mass spectrometer according to the embodiment of the present invention and measured values of logD obtained by measuring concentrations by a method using UV.

Particularly, when logD takes a high value in the range of approximately 4-6, logD can be measured more accurately. FIG. 6 is a plot of logD's measured with the mass spectrometer 15 and logD's measured with UV, for respective compounds. As shown in FIG. 6, the method of the invention allows us to measure the logD's of the samples for which the method with UV failed to measure the logD with sufficient accuracy (dots indicated by "UV>4" in the graph, and plotted as logD=5 for descriptive purposes) and the logD's of the samples for which the method with UV failed to measure the logD (dots indicated by "UV N. D." (Not Detected) in the graph, and plotted as logD=6 for descriptive purposes).

When the concentration in octanol 50$a$ is also obtained as in the present embodiment, it becomes feasible to calculate logD more accurately. When the concentration is measured by diluting octanol 50$a$ in consideration of the value of logD as in the present embodiment, logD can be accurately calculated even if the concentration in octanol 50$a$ is higher than the concentration in the buffer solution 50$b$.

The present embodiment showed the example in which the measurement of logD was carried out in the case where the buffer solution 50$b$ had the specific pH, but the method of the present invention is also applicable, for example, to calculation of logP based on measurement of logD's at different pHs of buffer solution 50$b$.

EXAMPLE 1

An example consistent with the above embodiment will be described below. The following tools, reagents, etc. were used in the present example.

well plate 12: 96 deep well plate (Agilent) (96 well Cap (Agilent) was also used as a cap of well plate 12)

octanol 50$a$: Wako special grade 1-Octanol

DMSO: DSMO pure solvent for UV absorption spectra (Dojindo)

ethanol: Wako EtOH for HPLC

Compounds used as objects for measurement of logD were those presented in Table 1 below.

TABLE 1

| 1 mM DMSO solution | 10 mM DMSO solution |
|---|---|
| Lidocaine | estradiol |
| Alprenolol | bifonazole |
| Antipyrine | Chlorpromazine |
| Metoprolol | Clozapine |
| Terbutaline | Imipramine |
| Acebutolol | Diltiazem |
| Carbamazepine | Chloramphenicol |
| Desipramine | Dexamethason |
| Propranolol | amiodarone |
| Trimethoprim | |

These compounds are ingredients of commercially available drugs and their logD's are known.

Figure 7:
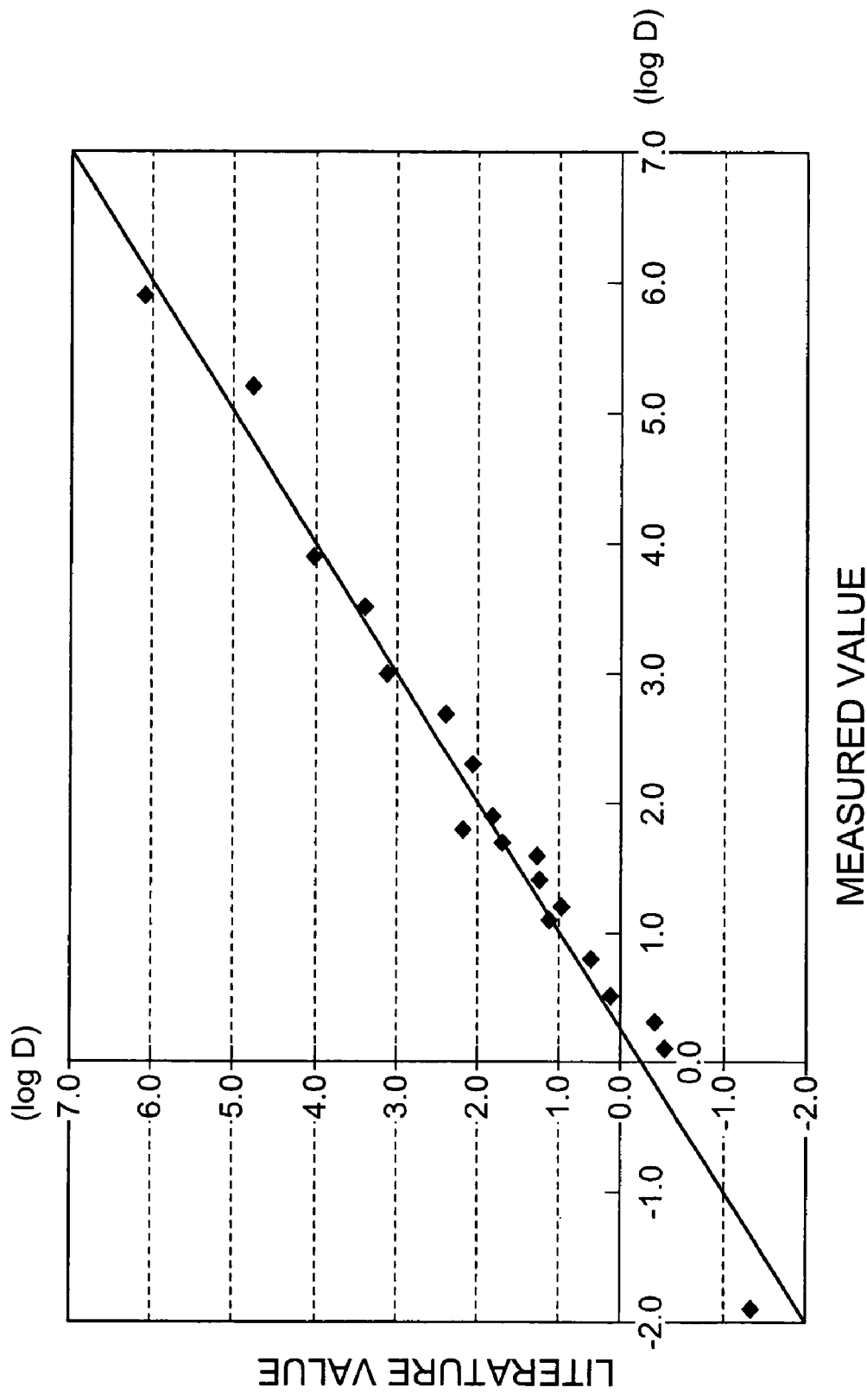
FIG. 7 is a scatter diagram of measured values of logD measured according to the embodiment of the invention, and literature values.

Table 2 below and the graph of FIG. 7 show measured values of logD of the respective compounds by the method according to the aforementioned present embodiment. The actually measured values presented in Table 2 and in the graph of FIG. 7 are average values of measured values in three measurements for each compound by the method according to the present embodiment, except for amiodarone (only one measurement for amiodarone).

TABLE 2

| Compound | Measured value | Literature value |
|---|---|---|
| Lidocaine | 1.7 | 1.71 |
| Alprenolol | 1.2 | 0.97 |
| Antipyrine | 0.5 | 0.38 |
| Metoprolol | 0.3 | −0.16 |
| Terbutaline | −1.9 | −1.35 |
| Acebutolol | 0.1 | −0.29 |
| Carbamazepine | 1.8 | 2.19 |
| Desipramin | 1.6 | 1.28 |

TABLE 2-continued

| Compound | Measured value | Literature value |
|---|---|---|
| Propranolol | 1.4 | 1.26 |
| Trimethoprim | 0.8 | 0.63 |
| estradiol | 3.9 | 4.01 |
| bifonazole | 5.2 | 4.77 |
| Chlorpromazine | 3.5 | 3.38 |
| Clozapine | 3.0 | 3.13 |
| Imipramine | 2.7 | 2.40 |
| Diltiazem | 2.3 | 2.06 |
| Chloramphenicol | 1.1 | 1.14 |
| Dexamethason | 1.9 | 1.83 |
| amiodarone | 5.9 | 6.10 |

The literature values shown in Table 2 and in the graph of FIG. 7 are those described in J. Med. Chem. 2001, 44, 2490-2497 (ElogDoct: A Tool for Lipophilicity Determination in Drug Discovery, 2. Basic and Neutral Compounds, Franco Lombardo, Marina Y. Shalaeva, Karl A. Tupper, and Feng Gao).

As shown in Table 2 and in the graph of FIG. 7, it is confirmed that the actually measured values are close to the literature values and that accurate logD's are obtained by the method of the present embodiment.

The invention claimed is:

1. A sampling method of sampling a lower-layer liquid from a liquid body comprised of two layers of liquids, an upper-layer liquid and the lower-layer liquid, using extracting means provided with a tubular apical end and adapted to bring the apical end from above into a liquid and to extract the liquid through the apical end, the sampling method comprising:

a plug injection step of injecting a plug liquid not mixing with the upper-layer liquid, into the apical end of the extracting means; and an extraction step of extracting the lower-layer liquid by means of the extracting means with the plug liquid injected in the plug injection step.

2. The sampling method according to claim 1, wherein the upper-layer liquid is octanol in which a predetermined chemical substance is dissolved, wherein the lower-layer liquid is a buffer solution in which the predetermined chemical substance is dissolved, and wherein the plug liquid is the buffer solution.

3. A logD measuring method of sampling a buffer solution from a liquid body comprised of two layers of liquids, an upper layer of octanol in which a predetermined chemical substance is dissolved, and a lower layer of the buffer solution in which the predetermined chemical substance is dissolved, using extracting means provided with a tubular apical end and adapted to bring the apical end from above into a liquid and to extract the liquid through the apical end, and measuring a logD of the chemical substance, the logD measuring method comprising:

a plug injection step of injecting a plug liquid not mixing with the octanol, into the apical end of the extracting means;

an extraction step of extracting the buffer solution by means of the extracting means with the plug liquid injected in the plug injection step;

an in-buffer concentration measuring step of measuring a concentration of the chemical substance in the buffer solution extracted in the extraction step; and a logD calculation step of calculating the logD on the basis of the concentration measured in the in-buffer concentration measuring step.

4. The logD measuring method according to claim 3, wherein a mass spectrometer is used to measure the concentration in the in-buffer concentration measuring step.

5. The logD measuring method according to claim 3, further comprising an in-octanol concentration measuring step of measuring a concentration of the chemical substance in the octanol, wherein the logD calculation step comprises calculating the logD on the basis of the concentrations measured in the in-buffer concentration measuring step and in the in-octanol concentration measuring step.

6. The logD measuring method according to claim 5, wherein the in-octanol concentration measuring step comprises extracting and diluting the octanol, and measuring a concentration of the chemical substance in the diluted octanol with a mass spectrometer, thereby measuring the concentration of the chemical substance.

7. A sampling apparatus for sampling a lower-layer liquid from a liquid body comprised of two layers of liquids, an upper-layer liquid and the lower-layer liquid, the sampling apparatus comprising:

extracting means provided with a tubular apical end and adapted to bring the apical end from above into a liquid and to extract the liquid through the apical end;

plug injecting means for injecting a plug liquid not mixing with the upper-layer liquid, into the apical end of the extracting means; and extraction controlling means for controlling the extracting means with the plug liquid injected by the plug injecting means, so as to extract the lower-layer liquid.

8. A logD measuring system for sampling a buffer solution from a liquid body comprised of two layers of liquids, an upper layer of octanol in which a predetermined chemical substance is dissolved, and a lower layer of the buffer solution in which the predetermined chemical substance is dissolved, and measuring a logD of the chemical substance, the logD measuring system comprising:

extracting means provided with a tubular apical end and adapted to bring the apical end from above into a liquid and to extract the liquid through the apical end;

plug injecting means for injecting a plug liquid not mixing with the octanol, into the apical end of the extracting means;

extraction controlling means for controlling the extracting means with the plug liquid injected by the plug injecting means, so as to extract the buffer solution;

in-buffer concentration measuring means for measuring a concentration of the chemical substance in the buffer solution extracted in the control by the extraction controlling means; and logD calculating means for calculating the logD on the basis of the concentration measured by the in-buffer concentration measuring means.

* * * * *